(12) United States Patent
Chudzik et al.

(10) Patent No.: US 7,547,445 B2
(45) Date of Patent: Jun. 16, 2009

(54) CROSSLINKABLE MACROMERS

(75) Inventors: Stephen J. Chudzik, St. Paul, MN (US); Joseph A. Chinn, Shakopee, MN (US)

(73) Assignee: SurModics, Inc., Eden Prairie, MN (US)

( * ) Notice: Subject to any disclaimer, the term of this patent is extended or adjusted under 35 U.S.C. 154(b) by 171 days.

(21) Appl. No.: 11/475,438

(22) Filed: Jun. 27, 2006

(65) Prior Publication Data

US 2006/0240072 A1    Oct. 26, 2006

(51) Int. Cl.
- A61F 2/02  (2006.01)
- A61F 2/06  (2006.01)
- A61F 2/28  (2006.01)
- A61F 13/00 (2006.01)

(52) U.S. Cl. ............ 424/422; 424/423; 424/427; 424/443; 424/445; 602/52; 623/1.46; 623/5.16; 623/6.62; 623/23.59; 623/920; 623/926

(58) Field of Classification Search ............ None
See application file for complete search history.

(56) References Cited

U.S. PATENT DOCUMENTS

| | | | |
|---|---|---|---|
| 3,879,353 A | 4/1975 | Crawford | 522/60 |
| 4,315,998 A | 2/1982 | Neckers | 525/332 |
| 4,477,326 A | 10/1984 | Lin | 528/15 |
| 4,594,400 A | 6/1986 | Kvita | 526/256 |
| 4,758,611 A | 7/1988 | Beers | 523/212 |
| 5,118,779 A | 6/1992 | Szycher | 528/75 |
| 5,213,580 A | 5/1993 | Slepian | 623/1 |
| 5,232,984 A | 8/1993 | Hubbell | 525/54 |
| 5,334,640 A | 8/1994 | Desai | 524/56 |
| 5,380,536 A | 1/1995 | Hubbell | 424/497 |
| 5,391,406 A | 2/1995 | Ramharack | 427/516 |
| 5,410,016 A | 4/1995 | Hubbell | 528/354 |
| 5,527,925 A | 6/1996 | Chabrecek | 549/430 |
| 5,529,914 A | 6/1996 | Hubbell | 435/182 |
| 5,552,452 A | 9/1996 | Khadem | 522/63 |
| 5,573,934 A | 11/1996 | Hubbell | 435/177 |
| 5,575,815 A | 11/1996 | Slepian | 623/1 |
| 5,612,050 A | 3/1997 | Rowe | 424/423 |
| 5,714,360 A * | 2/1998 | Swan et al. | 435/174 |
| 5,723,513 A | 3/1998 | Bonham | 522/63 |
| 5,843,156 A | 12/1998 | Slepian | 623/1 |
| 5,846,530 A | 12/1998 | Soon-Shiong | 424/93.7 |
| 5,858,746 A | 1/1999 | Hubbell | 435/177 |
| 5,900,245 A * | 5/1999 | Sawhney et al. | 424/426 |
| 6,007,833 A | 12/1999 | Chudzik | 425/425 |
| 6,093,302 A | 7/2000 | Montgomery | 205/122 |
| 6,156,345 A | 12/2000 | Chudzik | 424/484 |
| 6,410,044 B1 | 6/2002 | Chudzik | 424/423 |
| 6,558,665 B1 * | 5/2003 | Cohen et al. | 424/93.7 |
| 6,924,370 B2 | 8/2005 | Chudzik | 424/484 |
| 7,094,418 B2 * | 8/2006 | Chudzik et al. | 424/423 |
| 2005/0070688 A1 * | 3/2005 | Lewandowski et al. | 528/425 |
| 2005/0136091 A1 * | 6/2005 | Chudzik et al. | 424/423 |
| 2005/0192370 A1 * | 9/2005 | Fansler et al. | 522/1 |
| 2005/0281778 A1 * | 12/2005 | Park et al. | 424/78.27 |

FOREIGN PATENT DOCUMENTS

| | | |
|---|---|---|
| EP | 0 169 001 | 1/1986 |
| WO | WO 93/16687 | 9/1993 |
| WO | WO 96/40829 | 12/1996 |
| WO | WO 97/24376 | 7/1997 |

* cited by examiner

*Primary Examiner*—Jeffrey E Russel
(74) *Attorney, Agent, or Firm*—Pauly, Devries Smith & Deffner, L.L.C.

(57) ABSTRACT

A crosslinkable macromer system and related methods of preparing the system and using the system in the form of a crosslinked matrix between a tissue site and an implant article such as a tissue implant or on the porous surface of a prosthetic device. The macromer system includes two or more polymer-pendent polymerizable groups and one or more multifunctional initiator groups. The polymerizable groups and the initiator group(s), when polymer-pendent, can be pendent on the same or different polymeric backbones. The macromer system provides advantages over the use of polymerizable macromers and separate, low molecular weight initiators, including advantages with respect to such properties as non-toxicity, efficiency, and solubility. A macromer system of the invention can be used as an interface between the tissue site and implant article in a manner sufficient to permit tissue growth through the crosslinked matrix and between the tissue site and implant. In a preferred embodiment, polymers with pendent polymerizable groups, for use in the macromer system, are prepared by reacting a polysaccharide polymer with a reactive moiety in an organic, polar solvent such as formamide.

15 Claims, No Drawings

CROSSLINKABLE MACROMERS

CROSS REFERENCE TO RELATED APPLICATIONS

The disclosures of the following patents and applications are incorporated by reference herein: U.S. Ser. No. 10/990,582, filed Nov. 17, 2004, which is a continuation of U.S. Ser. No. 10/176,203, filed 20 Jun. 2002, which is a continuation of U.S. Ser. No. 09/571,525 (now U.S. Pat. No. 6,410,044), filed 16 May 2000, which is a continuation-in-part of U.S. Ser. No. 09/469,976 (now U.S. Pat. No. 6,156,345), filed 21 Dec. 1999, which is a divisional of U.S. patent application filed 23 Jul. 1998 and assigned Ser. No. 09/121,248 (now U.S. Pat. No. 6,007,833), which claims the benefit of provisional U.S. patent application filed 19 Mar. 1998 and assigned Ser. No. 60/078,607.

TECHNICAL FIELD

The present invention relates to the preparation of matrices by the polymerization of macromers. In another aspect, the invention relates to the use of such matrices for such purposes as cell immobilization, tissue adherence, and controlled drug delivery.

BACKGROUND OF THE INVENTION

Matrices are polymeric networks characterized by insolubility in water. One type of polymeric matrix is a hydrogel, which can be defined as a water-containing polymeric network. The polymers used to prepare hydrogels can be based on a variety of monomer types, such as those based on methacrylic and acrylic ester monomers, acrylamide (methacrylamide) monomers, and N-vinyl-2-pyrrolidone. To form the gel, these monomer classes are typically crosslinked with such crosslinking agents as ethylene dimethacrylate, N,N'-methylenebisacrylamide, methylenebis(4-phenyl isocyanate), ethylene dimethacrylate, divinylbenzene, and allyl methacrylate.

Another type of polymeric network can be formed from more hydrophobic monomers and/or macromers. Matrices formed from these materials generally exclude water. Polymers used to prepare hydrophobic matrices can be based on a variety of monomer types such as alkyl acrylates and methacrylates, and polyester-forming monomers such as $\epsilon$-caprolactone and lactide. When formulated for use in an aqueous environment, these materials do not need to be crosslinked, but they can be crosslinked with standard agents such as divinyl benzene. Hydrophobic matrices can also be formed from reactions of macromers bearing the appropriate reactive groups such as the reaction of diisocyanate macromers with dihydroxy macromers, and the reaction of diepoxy-containing macromers with dianhydride or diamine-containing macromers.

Although there exist a variety of methods for producing polymeric networks, when these networks are intended to be created in the presence of viable tissue, and/or to contain a bioactive compound, the number of acceptable methods of producing polymeric networks is extremely limited.

It is nevertheless desirable to form both hydrogel and non-hydrogel polymeric matrices in the presence of viable tissue or bioactive agents for the purposes of drug delivery, cellular immune isolation, prevention of post-surgical adhesions, tissue repair, and the like. These polymeric matrices can be divided into two categories: biodegradable or bioresorbable polymer networks and biostable polymer networks.

Biodegradable polymeric matrices have been previously suggested for a variety of purposes, including controlled release carriers, adhesives and sealers. When used as controlled release carriers, for instance, polymeric matrices can contain and release drugs or other therapeutic agents over time. Such matrices can be formed, for instance, by a number of different processes, including solvent casting hydrophobic polymers. Solvent casting, however, typically involves the use of organic solvents and/or high temperatures which can be detrimental to the activity of biological materials and can complicate production methods. Solvent casting of polymers out of solution also results in the formation of uncrosslinked matrices. Such matrices have less structure than crosslinked matrices and it is more difficult to control the release of bioactive agents from such matrices. Yet another process, which involves the polymerization of monomers in or around the desired materials, suffers from cytotoxicity of monomers, oxygen inhibition and heat of polymerization complications.

Another process used in the past to prepare biodegradable and biostable hydrogels involves the polymerization of pre-formed macromers using low molecular weight initiators. This process involves a number of drawbacks as well, however, including toxicity, efficacy, and solubility considerations. For instance, when using a macromer solution containing a low molecular weight soluble initiator to encapsulate viable cellular material, the initiator can penetrate the cellular membrane and diffuse into the cells. The presence of the initiator may involve some toxic consequence to the cells. When activated, however, these initiators produce free radicals having distinct cytotoxic potential. Other drawbacks arise if the initiator is able to diffuse out of the formed matrix, thereby producing toxicity and other issues. Such initiators also tend to aggregate in aqueous solution, causing efficiency and reproducibility problems. Finally, in view of the limited efficiency of many initiators for initiating the necessary radical chain polymerization, it is often necessary to add one or more monomeric polymerization "accelerators" to the polymerization mixture. Such accelerators tend to be small molecules capable of penetrating the cellular membrane, and often raise cytotoxic or carcinogenic concerns.

U.S. Pat. Nos. 5,410,016 (Hubbell, et al.) and 5,529,914 (Hubbell, et al.) for instance, relate to hydrogels prepared from biodegradable and biostable polymerizable macromers. The hydrogels are prepared from these polymerizable macromers by the use of soluble, low molecular weight initiators. Such initiators can be combined with the macromers, and irradiated in the presence of cells, in order to form a gel that encapsulates the cells. A considerable number of similar and related patents have arisen over recent years. See, for instance, U.S. Pat. Nos. 5,232,984; 5,380,536; 5,573,934; 5,612,050; 5,837,747; 5,846,530; and 5,858,746.

Hydrogels often suffer from similar or other drawbacks in use as biological adhesives or sealants, e.g., for use as tissue adhesives, endovascular paving, prevention of post-surgical adhesions, etc. In each of the applications, the hydrogel matrix must generally "adhere" to one or more tissue surfaces. Current methods rely upon physical "adhesion" or the tendency of hydrogels to "stick" to a surface. A superior adhesive would provide both physical and chemical adhesion to surfaces utilizing the same physical characteristics as current hydrogel adhesives, but also providing chemical, covalent coupling of the matrix material to the tissue surface. Covalent bonds are generally much stronger than physical adhesive forces, such as hydrogen bonding and van der Waals forces.

As described above, when various techniques are used to form polymeric matrices via photoinitiation of macromers, the photoinitiators utilized tend to be low molecular weight. Polymeric photoinitiators have been described as well, although for applications and systems quite distinct from those described above. See, for instance, "Radical Polymerization", C. H. Bamford, pp. 940-957 in Kroschwitz, ed., Concise Encyclopedia of Polymer Science and Engineering, 1990. In the subsection entitled "Photosensitized Initiation: Polymeric Photosensitizers and Photoinitiators", the author states that "[p]olymeric photosensitizers and photoinitiators have been described. Many of these are polymers based on benzophenone, e.g., poly(p-divinylbenzophenone) (DVBP). Such rigid polymers are reported to be effective sensitizers since hydrogen abstraction from the backbone by excited benzophenone is less likely."

U.S. Pat. No. 4,315,998 (Neckers) describes polymer-bound photosensitizing catalysts for use in the heterogeneous catalysis of photosensitized chemical reactions such as photo-oxidation, photodimerization, and photocyclo addition reactions. The polymer-bound photosensitizing catalysts are insoluble in water and common organic solvents, and therefore can be readily separated from the reaction medium and reaction products by simple filtration.

What is clearly needed are macromers and macromer systems that avoid the problems associated with conventional polymeric matrices, and in particular, those drawbacks that arise when polymeric matrices are formed in the presence of viable tissue or bioactive agents.

SUMMARY OF THE INVENTION

The present invention provides a method of improving the performance, within a host tissue site, of an implanted article (e.g., implanted tissue or implanted prosthetic device providing a porous surface), by promoting the growth of continuous tissue between host tissue and the implant. An implanted article of this invention can be provided, for instance, in the form of cultured tissue and/or native tissue (e.g., transplanted tissue), or can be fabricated from polymeric and/or metallic materials. The method employs a crosslinkable macromer system adapted to form an interface between the article and the host tissue, in order to facilitate (e.g., promote and/or permit) tissue integration by the body between the implant and the tissue site, e.g., into and through the crosslinked macromer and into the porosity of a porous device surface.

Applicant's parent application Ser. No. 09/121,248 (now U.S. Pat. No. 6,007,833) provides examples of preferred macromer systems useful in the method of the present invention. The parent application teaches the use of such systems for various applications, including cellular encapsulation, adhesives and sealants, barriers, controlled release carriers, tissue replacement/scaffolding, wound dressings, and in situ device formation. For use in tissue replacement, for instance, the parent application teaches the placement of a macromer system in a mold or cavities in a device.

Polymeric matrices of this invention (as formed by crosslinking the macromer system) can be used, for instance, to improve the tissue response to implanted medical devices. Examples of improved tissue response include: 1) increased tissue ingrowth (e.g., into the pores of cementless hip implants), 2) decreased absorbance of undesirable proteins and, 3) decreased fibrosis (e.g., around breast implants and hernia repair meshes). In addition to tissue integration, the macromer system can provide a variety of advantages, including a reduction in both immediate and chronic adverse reactions to the device (e.g., thereby preventing the accumulation of fluid and/or undesirable cells) by virtue of the immediate and desirable space filling characteristics.

A macromer system of this invention can be provided with a multifunctional initiator system comprising photoreactive molecules and hemocompatible molecules, e.g. fatty acids or lysine, in order to increase absorbance of desirable proteins, e.g. serum albumin, and to decrease absorbance of undesirable proteins e.g. fibrinogen. The multifunctional initiator system can be provided on the surface on an implant or adjacent to a tissue site in any suitable manner, can be polymerized to form a matrix at any suitable time, e.g. the macromer system and multifunctional initiator system can be coated on an implant, and/or delivered to the tissue site and crosslinked either before, during and/or after positioning the implant in the tissue site.

A macromer system of this invention can be provided between the implant and tissue site in any suitable manner, e.g., the system can be provided upon the surface of the implant before, during and/or after placement of the implant in the tissue site. Similarly, the macromer system(s) can be polymerized to form a matrix at any suitable point, e.g., a system can be coated on an implant, and/or delivered to the tissue site, and crosslinked either before, during and/or after positioning the implant in or upon the tissue site. For example, a system can be provided and crosslinked on the surface of a prosthetic device, e.g., by either the manufacturer or surgeon, and implanted into the tissue site. As another example, a macromer system can be applied to the tissue site itself, polymerized in situ (e.g., by the application of illumination either directly to the system or through translucent tissue), and an implant article (with or without a macromer system or matrix on its surface) positioned on or in the site.

The resulting combination of implant and matrix within the tissue site, permits the formation of continuous tissue growth, over time, through the matrix and between the implant and tissue site. Such growth can be unidirectional (e.g., originating from the tissue site toward the implant) and/or bidirectional (e.g., originating from both the tissue site and from an implanted tissue).

A system, or resultant matrix, can be applied with or without additional components, such as growth factors, morphogenic factors, or DNA. Both degradable and non-degradable macromer systems are useful, but matrices adapted to degrade with desired kinetics, are preferred.

In another aspect, the present invention provides a combination comprising an implant article, such as a tissue implant or prosthetic device having one or more porous surfaces, and a matrix formed of a crosslinked macromer system as described herein. In one embodiment, the article and uncrosslinked macromer system are initially combined (e.g., the system coated on the article) outside the body, thereby permitting the system to be crosslinked prior to, during and/or following placement of the implant within the body site. In an alternative embodiment, the combination is provided by positioning an article within and/or in apposition to the body site, and delivering the macromer system to the body site (before, during and/or after placement of the article itself), where it is crosslinked as a sufficiently stable coating or other suitable interface in its position between the article and the tissue site.

For instance, a macromer system in liquid (e.g., substantially flowable) form can be applied to a tissue defect, before, during or after which a tissue implant or preformed device is pressed into the defect. The system can be provided, for instance, to occupy a space of between about 0.1 mm to about 10 mm between the implant and the tissue site. The system is illuminated in order to activate the initiator groups and thus polymerize the macromer system into a solid matrix. The resultant combination of tissue implant or preformed device, together with crosslinked macromer system, completely and conformally fills the defect such that no gaps remain for the accumulation of undesirable fluids or cells.

As described herein, the macromer system can thus be used in the manner of a "grout", for instance, to fill the spaces between a tissue implant or preformed device (itself either tissue-based or non-tissue based) and adjacent tissue. Current tissue implants include, for instance, both those obtained as transplants (e.g., autografts, allografts or xenografts) and those provided by tissue engineering. Current tissue engineering products often consist of cultured tissues that are implanted into tissue defects. Such products do not typically conform well to adjacent native tissue, however, thus leaving spaces into which undesirable fluids and cells can accumulate and produce adverse tissue responses. For example, when cultured cartilage is implanted into cartilage defects, synovial fluid and macrophages can enter the unfilled space and lead to fibrous tissue formation, which prevents integration of the implanted cartilage with the native cartilage. Other cultured tissues that are implanted into tissue defects, and that would benefit from the present macromer system applied as a grout include, but are not limited to, skin, bone, ligaments, blood vessels, and heart valves.

Implants, e.g., prosthetic devices, useful in a combination or method of this invention include those in which tissue integration is desired, and that themselves provide (or can be provided with) a sufficiently porous surface that permits or facilitates tissue integration once positioned in vivo. Examples of suitable porous prosthetic devices include, but are not limited to; joint implants (e.g., for hip or knee reconstruction), dental implants, soft tissue cosmetic prostheses (e.g., breast implants), wound dressings, vascular prostheses (e.g., vascular grafts and stents), and ophthalmic prostheses (e.g., intracorneal lenses). The macromer system of this invention, in turn, can be used in any suitable manner, e.g., to coat and/or fill voids within or upon the surface of the prosthetic device.

Such devices preferably are themselves formed of or otherwise provide (or can be provided with) a surface having sufficient porosity to permit tissue ingrowth in vivo. As used herein, the word "porous", and inflections thereof, will refer to one or more portions of the device surface that are designed for direct or indirect contact with the surrounding natural tissue, sufficient to permit tissue integration into the porosity thereof. Porous surfaces can be provided in a variety of ways, e.g., as sintered particles on a surface, such as titanium particles on the surface of cementless hip implants, as are available from a variety of orthopedic companies. Porous surfaces can also be provided in the form of cavities that remain from mixing salt crystals with silicone rubber oligomers, then solidifying (vulcanizing) the silicone rubber, and finally dissolving the salt crystals (as currently done for a variety of breast implants). Yet other porous surfaces can be fabricated from fibrous materials or produced as porous sponges via solvent casting and particulate leaching, phase separation, or gas foaming (see, e.g., B. S. Kim and D. J. Mooney, Development of Biocompatible Synthetic Extracellular Matricies for Tissue Engineering TIBTECH 16:224-230 (1998).

Such porous surfaces typically provide a three-dimensional structure of spaces into which tissue can grow and mature. Porous regions of an implantable device preferably have a high pore density, in that the pores themselves occupy a greater relative volume than the material forming and separating those pores. Desirably, the pores have interconnected passages that allow direct contact between the tissue growing in adjacent pores. The minimum average pore size is preferably sufficient to accommodate capillaries (e.g., of about 5 micron diameter) and the maximum average pore size is about 1 mm. Preferable pore sizes will vary from tissue to tissue and typically range from about 20 microns to about 600 microns, and more preferably from about 50 microns to about 400 microns.

A crosslinkable macromer system useful in the present invention comprises two or more polymer-pendent polymerizable groups and one or more initiators, preferably in the form of polymer-pendent initiator groups. In a preferred embodiment, the polymerizable groups and the initiator group(s) are pendent on the same polymeric backbone. In an alternative preferred embodiment, the polymerizable groups and initiator group(s) are pendent on different polymeric backbones.

In the first embodiment, the macromer system comprises a polymeric backbone to which are covalently bonded both the polymerizable groups and initiator group(s). Pendent initiator groups can be provided by bonding the groups to the backbone at any suitable time, e.g., either prior to the formation of the macromer (for instance, to monomers used to prepare the macromer), or to the fully formed macromer itself. The macromer system itself will typically comprise but a small percentage of macromers bearing both initiator groups and polymerizable groups. The majority of macromers will provide only pendent polymerizable groups, since the initiator groups are typically sufficient if present at far less than 1:1 stoichiometric ratio with macromer molecules.

In an alternative preferred embodiment, the macromer system comprises both polymerizable macromers, generally without pendent initiator groups, in combination with a multifunctional polymeric initiator. In either embodiment, the initiator will be referred to herein as a "polymeric initiator", by virtue of the attachment of such initiator groups to a polymeric backbone, for example, the latent reactive groups attached to a polymeric backbone described in U.S. Pat. Nos. 5,002,582 and 6,121,027, herein incorporated by reference in its entirety and are commonly owned by the assignee. Yet another embodiment of this invention includes the macromer system having free (non-polymer bound) initiator molecules. The free non-polymer bound initiator moieties are either non-polymeric or monomeric as well as multifunctional in character. In a preferred embodiment, the free non-polymer bound initiators are based on moieties that contain at least one latent reactive group as described in U.S. Pat. No. 6,465,525, and US 2003/0165613, which are all incorporated by reference in their entirety and are all commonly owned by the assignee. Free non-polymer bound initiator systems can initiate polymerization of a macromer system either alone when activated or in combination with a polymeric initiator.

Macromer systems of the present invention, employing polymeric initiators, provide a number of unexpected advantages over the use of polymerizable macromers and separate, low molecular weight initiators. Such systems, for instance, provide an optimal combination of such properties as non-toxicity, efficiency, and solubility. Solubility, for instance, can be improved by virtue of the ability to control the aqueous or organic solubility of the polymerizable macromer by controlling the backbone. Toxicity can also be improved, since the polymeric initiators of this invention typically cannot diffuse into cells in the course of immobilization.

In a preferred embodiment, the pendent initiator groups are selected from the group consisting of long-wave ultra violet (LWUV) light-activatable molecules such as; 4-benzoylbenzoic acid, [(9-oxo-2-thioxanthanyl)-oxy]acetic acid, 2-hydroxy thioxanthone, and vinyloxymethylbenzoin methyl ether; visible light activatable molecules; eosin Y, rose bengal, camphorquinone and erythrosin, and thermally activatable molecules; 4,4'azobis(4-cyanopentanoic) acid and 2,2- azobis[2-(2-imidazolin-2-yl) propane] dihydrochloride. An important characteristic of the initiator group being the ability to be coupled to a preformed macromer containing polymerizable groups, or to be modified to form a monomer which can take part in the macromer synthesis, which is subsequently followed by the addition of polymerizable groups.

In such an embodiment, the pendent polymerizable groups are preferably selected from the group consisting of pendent vinyl groups, acrylate groups, methacrylate groups, ethacrylate groups, 2-phenyl acrylate groups, acrylamide groups, methacrylamide groups, itaconate groups, and styrene groups.

In a further preferred embodiment, the polymeric backbone is selected from the group consisting of synthetic macromers, such as polyvinylpyrrolidone (PVP), polyethylene oxide (PEO), and polyethylene glycol (PEG); derivatizable naturally occurring polymers such as cellulose; polysaccharides, such as hyaluronic acid, dextran, and heparin; and proteins, such as collagen, gelatin, and albumin.

The macromers of the present invention can be used in a variety of applications, including controlled drug release, the preparation of tissue adhesives and sealants, the immobilization of cells, and the preparation of three-dimensional bodies for implants. In one aspect, for instance, the invention provides a method for immobilizing cells, the method comprising the steps of combining a polymeric initiator of the present invention with one or more polymerizable macromers and in the presence of cells, under conditions suitable to polymerize the macromer in a manner that immobilizes the cells.

DETAILED DESCRIPTION

As used herein the following words and terms shall have the meaning ascribed below:

"macromer system" shall refer to a polymerizable polymer system comprising one or more polymers providing pendent polymerizable and initiator groups. Groups can be present either on the same or different polymeric backbones, e.g., on either a polymerizable macromer or a non-polymerizable polymeric backbone;

"polymerizable macromer" shall refer to a polymeric backbone bearing two or more polymerizable (e.g., vinyl) groups;

"multifunctional" shall refer to a chemical system that can provide a combination of desirable chemical and biocompatible properties. A multifunctional system comprises chemical molecules, or combinations of chemical molecules, that are capable of initiating a free radical reaction and reducing immediate and chronic adverse reactions to an implanted medical device. Examples of a multifunctional chemical system are chemical molecules comprising both a photoreactive group and a hemocompatible group or a photoreactive group and a charged group.

"initiator group" shall refer to one or more chemical groups capable of initiating a free radical reaction, present as either a pendent group on a polymerizable macromer, pendent on a separate, non-polymerizable polymer backbone, or free non-polymer bound moieties that are either non-polymeric or monomeric as well as multifunctional in character; and "polymeric initiator" shall refer to a polymeric backbone (polymerizable or non-polymerizable) comprising one or more initiator groups and optionally containing one or more other thermochemically reactive groups or affinity groups.

The polymeric backbone of this invention can be either synthetic or naturally-occurring, and includes a number of macromers previously described as useful for the preparation of polymeric matrices. Generally, the backbone is one that is soluble, or nearly soluble, in aqueous solutions such as water, or water with added organic solvent (e.g., dimethylsulfoxide) or can be rendered soluble using an appropriate solvent or combination of solvents. Alternatively, the polymeric backbone can be a material which is a liquid under ambient physiological conditions. Backbones for use in preparing biodegradable gels are preferably hydrolyzable under in vivo conditions.

In general, the polymeric backbones of this invention can be divided into two categories: biodegradable or bioresorbable, and biostable reagents. These can be further divided into reagents which form hydrophilic, hydrogel matricies and reagents which form non-hydrogel matricies.

Bioresorbable hydrogel-forming backbones are generally naturally occurring polymers such as polysaccharides, examples of which include, but are not limited to, hyaluronic acid (HA), starch, dextran, heparin, chondroitin sulfate, dermatan sulfate, heparan sulfate, keratan sulfate, dextran sulfate, pentosan polysulfate, and chitosan; and proteins (and other polyamino acids), examples of which include but are not limited to gelatin, collagen, fibronectin, laminin, albumin, elastin, and active peptide domains thereof. Matrices formed from these materials degrade under physiological conditions, generally via enzyme-mediated hydrolysis.

Hyaluronic acid, when derivatized with polymerizable groups in the manner described herein, provides a variety of advantages and benefits not heretofore known or achievable. Hyaluronic acid has conventionally been derivatized in aqueous conditions (see, e.g., Soon-Shiong (U.S. Pat. No. 5,837,747), Sakurai (U.S. Pat. No. 4,716,224), and Matsuda (U.S. Pat. No. 5,763,504). Occasional references have described the ability to derivatize hyaluronic acid under organic conditions (see, e.g., Della Valle, U.S. Pat. No. 5,676,964). In most, if not all, such approaches, however, the reaction mixtures are either suspensions, as opposed to true solutions, or the hyaluronic acid is itself pre-reacted (typically in a predominantly aqueous mixture) to enhance its solubility in organic solvents.

Applicants have discovered the manner in which hyaluronic acid, as well as other polysaccharides and polyamino acids (such as collagen) can be effectively derivatized in organic, polar, anhydrous solvents and solvent combinations. A particularly preferred solvent is formamide, and combinations of other solvents therewith. Functionally, the solvent or solvent system is one in which the polymer is sufficiently soluble and that permits its derivatization to the desired extent. The ability to derivatize such polymers in the manner of this invention provides a variety of unexpected benefits, and an optimal combination of such properties as preparation cost, controllability, and yield.

As exemplified below, for instance, hyaluronic acid is reacted in formamide (and TEA, for pH control) with a reactive moiety in the form of glycidyl acrylate in order to derivatize the hyaluronic acid molecules with acrylate groups. The number and/or density of acrylate groups can be controlled using the present method, e.g., by controlling the relative concentration of reactive moiety to saccharide group content.

Bioresorbable matrix-forming backbones are generally synthetic polymers prepared via condensation polymerization of one or more monomers. Matrix-forming polymers of this type include polylactide (PLA), polyglycolide (PGA), polycaprolactone (PCL), as well as copolymers of these materials, polyanhydrides, and polyortho esters.

Biostable hydrogel matrix-forming backbones are generally synthetic or naturally occurring polymers which are soluble in water, matrices of which are hydrogels or water-containing gels. Examples of this type of backbone include polyvinylpyrrolidone (PVP), polyethylene glycol (PEG), polyacrylamide (PAA), polyvinyl alcohol (PVA), and the like.

Biostable matrix-forming backbones are generally synthetic polymers formed from hydrophobic monomers such as methyl methacrylate, butyl methacrylate, dimethyl siloxanes, and the like. These backbone materials generally do not possess significant water solubility but can be formulated as neat liquids which form strong matrices upon activation. It is also possible to synthesize backbone polymers which contain both hydrophilic and hydrophobic monomers.

Polymeric backbones of polymerizable macromers can optionally provide a number of desirable functions or attributes, e.g., as described in the above-captioned Hubbell patents, the disclosures of which are incorporated herein by reference. Backbones can be provided with water soluble regions, biodegradable regions, hydrophobic regions, as well as polymerizable regions.

As used herein, the term "polymerizable group" will generally refer to a group that is polymerizable by initiation by free radical generation, most preferably by photoinitiators activated by visible or long wavelength ultraviolet radiation. Preferred polymerizable groups include acrylates, methacrylates, ethacrylates, itaconates, acrylamides, methacrylamide, and styrene.

Typically, polymerizable groups are incorporated into a macromer subsequent to the initial macromer formation using standard thermochemical reactions. Thus, for example, polymerizable groups can be added to collagen via reaction of amine containing lysine residues with acryloyl chloride or glycidyl acrylate. These reactions result in collagen containing pendent polymerizable moieties. Similarly, when synthesizing a macromer for use as described in the present invention, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups.

Initiator groups useful in the system of the present invention include those that can be used to initiate, by free radical generation, polymerization of the macromers to a desired extent and within a desired time frame. Crosslinking and polymerization are generally initiated among macromers by a light-activated free-radical polymerization initiator. Any dye can be used which absorbs light having frequency between 320 nm and 900 nm, can form free radicals, is at least partially water soluble, and is non-toxic to the biological material at the concentration used for polymerization. Examples of suitable dyes are eosin Y, fluorescein, 2-methoxy, 2-phenylacetophenone, rose bengal, methylene blue, erythrosin, phloxime, thionine, riboflavin and methylene green. Preferred initiators for long wave UV and visible light initiation include ethyl eosin, 2,2-dimethoxy-2-phenyl acetophenone, other acetophenone derivatives, thioxanthone, benzophenone, quinone, and camphorquinone.

Preferred polymeric initiators are photosensitive molecules which capture light energy and initiate polymerization of the macromers. Other preferred polymeric initiators are thermosensitive molecules which capture thermal energy and initiate polymerization of the macromers. Additionally preferred are free non-polymer bound initiators that are non-polymeric, or monomeric in character. Such free non-polymer bound initiators are based on moieties that contain at least one latent reactive group. Latent reactive groups are those groups of atoms in a molecule which retain their covalent bonds unchanged under conditions of storage but which, upon activation, form covalent bonds with other molecules or incite polymerization of macromer systems. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups as described are generally well known.

In one embodiment, free non-polymer bound initiators, as characterized by nonpolymeric moieties, are defined as comprising at least one photoinitiator group and preferably at least one or more latent reactive (e.g. photoreactive) groups adapted to be activated in order to covalently attach to a surface. An initiator of this type comprises a chemical non-polymeric core molecule having attached to it one or more first latent reactive groups and one or more second latent reactive groups, each of the first and second latent reactive groups being attached to the backbone in such a manner that, upon activation of the latent reactive groups in the presence of a support surface, a) the first latent reactive groups are capable of covalently bonding to the support surface, and
b) upon bonding of the first latent reactive groups to the surface, the second latent reactive groups are;
   i) restricted from reacting with either a spacer or the support surface,
   ii) capable of reverting to their inactive state, and
   iii) upon reverting to their inactive state, are thereafter capable of being reactivated in order to later initiate polymerization of macromers, thereby forming a macromer on the surface.

The first and second latent reactive groups can be of the same or different types, and as previously, the distinction between the two can be determined under the conditions, and at the time of use. Generally, the first latent reactive groups are defined (from amongst those originally present) as those that become attached to the surface itself, which in turn, serves to define the second latent reactive groups as those that remain unattached, and hence revert to activatable form. In the present invention, Applicants have found that those second latent reactive groups are particularly well suited to serve as photoinitiators for a polymerization reaction. In a particularly preferred embodiment, the free non-polymer bound initiator of the invention is selected from the group consisting of tetrakis (4-benzoylbenzyl ether), the tetrakis (4-benzoylbenzoate ester) of pentaerythritol, and an acylated derivative of tetraphenylmethane In an alternative embodiment, the free non-polymer bound initiator provides an initiator system comprising a nonpolymeric core molecule having attached thereto, either directly or indirectly, one or more substituents comprising negatively charged groups, and two or more latent reactive species, wherein the latent reactive species are provided as discrete latent reactive groups. In such an embodiment, the latent reactive species comprise one or more first latent reactive species adapted to attach the coating agent to a surface, and one or more second latent reactive (e.g., photoreactive) species adapted to initiate photopolymerization. Suitable reagents of this type are described, for instance, in Applicants' U.S. Pat. No. 6,669,994 the disclosure of which is incorporated herein by reference.

In one such embodiment, the coating agent comprises a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical. Preferably, the conjugated cyclic diketone is a quinone selected from substituted and unsubstituted benzoquinone, camphorquinone, naphthoquinone, quinone, and anthraquinone.

Such reagents typically comprise a nonpolymeric core molecule having attached thereto, either directly or indirectly, one or more substituents comprising negatively charged groups, and two or more latent reactive species, wherein the latent reactive species are provided as discrete photoreactive groups. In a preferred embodiment, such coating agents are selected from the group 4,5-bis(4-benzoylphenylmethyleneoxy) benzene-1,3-disulfonic acid dipotassium salt (DBDS), 2,5-bis(4-benzoylphenylmethyleneoxy) benzene-1,4-disulfonic acid dipotassium salt (DBHQ), a hydroquinone monosulfonic acid derivative, an anthraquinone sulfonic acid salt, and a camphorquinone derivative. Optimally, the coating agent is selected from DBDS, DBHQ, and 2,5-bis(4-benzoylphenylmethyleneoxy) benzene-1-sulfonic acid mono (or di-) sodium salt.

Particularly preferred free non-polymer bound initiator groups of this type are selected from the group 4,5-bis(4-benzoylphenylmethyleneoxy) benzene-1,3-disulfonic acid dipotassium salt (DBDS), and 2,5-bis(4-benzoylphenylmethyleneoxy) benzene-1,4-disulfonic acid dipotassium salt (DBHQ).

In another alternative embodiment, an initiator groups can be provided in the form of the general formula:

wherein each X is independently a radical containing a latent reactive (e.g., photoreactive) group and Y is a radical containing one or more charged groups. Such embodiments are described, for instance, in Applicant's U.S. Pat. No. 5,714,360, the disclosure of which is incorporated herein by reference.

An initiator group of this type includes one or more charged groups, and optionally one or more additional latent reactive (e.g., photoreactive) groups, included in the radical identified in the empirical formula as "Y." A "charged" group, when used in this sense, refers to groups that are present in ionic form, i.e., carry an electrical charge under the conditions (e.g., pH) of use. The charged groups are present, in part, to provide the compound with the desired water solubility.

Preferred Y groups are nonpolymeric, that is, they are not formed by polymerization of any combination of monomers. Nonpolymeric agents are preferred since they will tend to have lower molecular mass, which in turn means that they can generally be prepared to have a higher concentration of latent reactive groups per unit mass. In turn, they can generally provide a higher coating density of latent reactive groups than comparable latent reactive polymeric agents.

The type and number of charged groups in a preferred agent are sufficient to provide the initiator group with a water solubility (at room temperature and optimal pH) of at least about 0.1 mg/ml, and preferably at least about 0.5 mg/ml, and more preferably at least about 1 mg/ml. Given the nature of the surface coating process, linking agent solubility levels of at least about 0.1 mg/ml are generally adequate for providing useful coatings of target molecules on surfaces.

Examples of suitable charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. An example of an agent employing charged groups other than quaternary ammonium compounds is provided in Formula X of Table I in the '360 patent. By reference to the empirical formula provided above, it can be seen that $R^3$ in Formula X would be a lone pair of electrons, in order to provide a tertiary amine group, and $R^2$ would contain a charged sulfonate group in a radical of the formula —$CH_2$—$CH_2$—$SO_3Na$. Sufficient overall charge to render the compound water soluble is provided by the negative charge of the remote sulfonate group.

A preferred charged group for use in preparing compounds of this initiator group is a quaternary ammonium group. The term "quaternary ammonium," as used herein, refers to organic derivatives of $NH_4^+$ in which the hydrogen atoms are each replaced by radicals, thereby imparting a net positive charge on the radical. The remaining counter-ion can be provided by any suitable anionic species, such as a chloride, bromide, iodide, or sulfate ion.

In a preferred embodiment two or more photoreactive groups are provided by the X groups attached to the central Y radical. Upon exposure to a suitable light source, each of the photoreactive groups are subject to activation. The term "photoreactive group," as used herein, refers to a chemical group that responds to an applied external ultraviolet or visible light source in order to undergo active specie generation, resulting in covalent bonding to an adjacent chemical structure (via an abstractable hydrogen) and polymerization initiation of the macromer system.

Preferred initiators of this type are selected from the group ethylenebis(4-benzoylbenzyldimethylammonium) dibromide (Diphoto-Diquat); hexamethylenebis(4-benzoylbenzyldimethylammonium) dibromide (Diphoto-Diquat); 1,4-bis(4-benzoylbenzyl)-1,4-dimethylpiperazinediium dibromide (Diphoto-Diquat); bis(4-benzoylbenzyl) hexamethylenetetraminediium dibromide (Diphoto-Diquat); bis[2-(4-benzoylbenzyldimethylammonio)ethyl]-4-benzoylbenzylmethylammonium tribromide (Triphoto-Triquat); 4,4-bis(4-benzoylbenzyl)morpholinium bromide (Diphoto-Monoquat); ethylenebis[(2-(4-benzoylbenzyldimethylammonio)ethyl)-4-benzoylbenzylmethylammonium] tetrabromide (Tetraphoto-Tetraquat); 1,1,4,4-tetrakis(4-benzoylbenzyl) piperazinediium Dibromide (Tetraphoto-Diquat); and N,N-bis[2-(4-benzoylbenzyloxy)ethyl]-2-aminoethanesulfonic acid, sodium salt (Diphoto-Monosulfonate), and analogues (including those having alternative counter ions) thereof, corresponding to Compounds II through X, respectively, of the above-captioned '360 patent. Terms such as "Diphoto-Diquat" are used herein to summarize the number of respective groups (e.g., photo groups, quaternary ammonium groups, etc.) per initiator molecule.

In another embodiment, free non-polymer bound initiators are characterized as comprising a latent reactive group and a bifunctional aliphatic acid, in combination with a spacer group linking the latent reactive group to the aliphatic acid. In a preferred embodiment, the initiator group is of the general formula:

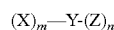

where X is a latent reactive (e.g., photoreactive) group, Y is a spacer radical, and Z is a bifunctional aliphatic acid, as each are described herein. The values of m and n are >=1 and while m can equal n, it is not necessary. The aliphatic acid is 'bifunctional' in that it provides both an aliphatic region and an anionic (e.g., carboxylic acid) region.

In a preferred embodiment where both m and n=1, the initiator group is termed a heterobifunctional initiator group. The aliphatic acid is preferably attached to the latent reactive group by means of a divalent spacer group in a manner that does not detrimentally affect the function of either the aliphatic or anionic portions. Higher-valent spacer groups can also be selected which permit the attachment of multiple aliphatic acid and latent reactive groups, again in a manner which does not detrimentally affect the functions of the respective groups. In this case m does not necessarily equal n and both are >=1.

The bifunctional aliphatic acid of the present invention ("Z" group) includes both an aliphatic portion and an anionic portion. The word "aliphatic", as used herein, refers to a substantially linear portion, e.g., a hydrocarbon backbone. The word "anionic", in turn, refers to a charged portion.

In a preferred embodiment, the initiator group includes photoactivatible molecules having fatty acid functional groups, including polymers having multiple photoactivatible and fatty acid functional groups, as well as heterobifunctional molecules. Photoactivatible polyacrylamide copolymers containing multiple pendant fatty acid analogs and multiple pendant photogroups have been synthesized from acrylamide, a benzophenone-substituted acrylamide, and N-substituted acrylamide monomers containing the fatty acid analog. Photoactivatible polyvinylpyrrolidones have also been prepared in a similar fashion. Polyacrylamide or polyvinylpyrrolidone copolymers with a single end-point photogroup and multiple pendant fatty acid analogs have also been synthesized. Finally, photoactivatible, heterobifunctional molecules having a benzophenone on one end and a fatty acid group on the other end optionally separated by a spacer have been made, wherein that spacer can be a hydrophobic alkyl chain or a more hydrophilic polyethyleneglycol (PEG) chain.

Suitable spacers ("Y" groups) for use in preparing heterobifunctional initiator groups include any di- or higher-functional spacers capable of covalently attaching a latent reactive group to an aliphatic acid in a manner that permits them both to be used for their intended purpose. Although the spacer may itself provide a desired chemical and/or physical function, preferably the spacer is non-interfering, in that it does not detrimentally affect the use of the aliphatic and ionic portions for their intended purposes. The spacer may be aliphatic and contain various heteroatoms such as O, N, and S in place of carbon. Constituent atoms of the spacers need not be aligned linearly. For example, aromatic rings, which lack abstractable hydrogen atoms (as defined below), can be included as part of the spacer design in those initiators where the latent reactive group functions by initiating covalent bond formation via hydrogen atom abstraction. In its precursor form (i.e., prior to attachment of a photoreactive group and aliphatic acid), a spacer can be terminated with any suitable functionalities, such as hydroxyl, amino, carboxyl, and sulfhydryl groups, which are suitable for use in attaching a photoreactive group and the aliphatic acid by a suitable chemical reaction, e.g., conventional coupling chemistry.

Alternatively, the spacer can be formed in the course of combining a precursor containing (or capable of attaching) the photoreactive group with another precursor containing (or capable of attaching) the aliphatic acid. For example, the aliphatic acid could be reacted with an aliphatic diamine to give an aliphatic amine derivative of the bifunctional aliphatic acid and which could be coupled with a carboxylic acid containing the photogroup. To those skilled in the art, it would be obvious that the photogroup could be attached to any appropriate thermochemical group which would react with any appropriate nucleophile containing O, N or S.

Examples of suitable spacer groups include, but are not limited to, the groups consisting of substituted or unsubstituted alkylene, oxyalkylene, cycloalkylene, arylene, oxyarylene, or aralkylene group, and having amides, ethers, and carbonates as linking functional groups to the photoactivatible group, and the bifunctional aliphatic fatty acid.

In a preferred embodiment one or more photoreactive groups are provided by the X groups attached to the central Y spacer radical. Upon exposure to a suitable light source, each of the photoreactive groups are subject to activation. The term "photoreactive group", as used herein, refers to a chemical group that responds to an applied external energy source in order to undergo active specie generation, resulting in the initiation of polymerization for the macromer system.

Preferred X groups are sufficiently stable to be stored under conditions in which they retain such properties, as described in U.S. Pat. No. 5,002,582. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones are preferred, such as acetophenone, benzophenone, anthraquinone, quinone, anthrone, and anthrone-like heterocycles (i.e., heterocyclic analogues of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (for example, from a support surface or target molecule in the solution and in bonding proximity to the agent), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are particularly preferred.

Photoinitiation of the free radical polymerization of macromers of the present invention will generally occur by one of three mechanisms. The first mechanism involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone.

The second mechanism involves a hydrogen abstraction reaction, either intra- or intermolecular. This initiation system can be used without additional energy transfer acceptor molecules and utilizing nonspecific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, and camphorquinone.

When using a polymeric initiator of the hydrogen abstraction variety, pendent tertiary amine groups can be incorporated into the polymeric backbone of the macromer. This will insure that all free radicals formed are polymer-bound.

The third mechanism involves photosensitization reactions utilizing photoreducible or photo-oxidizable dyes. In most instances, photoreducible dyes are used in conjunction with a reductant, typically, a tertiary amine. The reductant intercepts the induced triplet producing the radical anion of the dye and the radical action of the reductant. Examples of molecules exhibiting photosensitization reactivity and useful in a polymeric initiating system include eosin Y, rose bengal, and erythrosin. Reductants can be incorporated into the polymer backbone, thereby assuring that all free radicals will be polymer-bound.

Thermally reactive polymeric initiators are also useful for the polymerization of macromers. Examples of thermally reactive initiators usable in a polymeric initiating system include 4,4' azobis(4-cyanopentanoic acid) and analogs of benzoyl peroxide.

A surprisingly beneficial effect of the use of polymeric initiators to polymerize macromers is the increased efficiency of polymerization exhibited by these polymeric initiators as compared to their low molecular weight counterparts. This increased efficiency is seen in all three photoinitiation mechanisms useful for the polymerization of macromers.

Polymeric initiation of monomer solutions has been investigated for its application in the field of UV-curable coatings for industrial uses, c.f. U.S. Pat. No. 4,315,998 (Neckers) and PCT Application, International Publication No. WO 97/24376 (Kuester, et. al.) but there have been no reports of the adaptation of the use of polymeric initiators for the polymerization of macromers in the presence of biologic material or for the creation of drug-releasing matrices.

High efficiency of initiation is particularly important in systems such as these. It is generally desirable, when forming polymeric matrices in the presence of biologic or bioactive materials, to minimize the exposure time of the material to the energy source used to initiate polymerization. It is therefore imperative that the initiation system utilized possess optimum initiation efficiency.

When matrix strength or durability are required for a particular application, high efficiency is again a necessary characteristic of an initiation system. When a matrix-forming system is initiated, the free radical polymerization of the system is propagated until gelation and vitrification of the polymerizing system render the diffusion of the elements of the matrix-forming system too difficult. Therefore, the higher the efficiency of the initiation system, the more complete the polymerization resulting in the formation of stronger, more durable matrices. The polymeric initiation systems described in this invention provide a higher degree of efficiency, with or without the use of accelerants, than is attainable using non-polymer-bound, low molecular weight initiators.

Another beneficial effect is realized when the initiating groups on the polymeric initiators consist of groups exhibiting hydrogen abstraction reactivity, i.e., the ability to abstract hydrogens intermolecularly. The beneficial effect is important when macromer systems containing these initiators are used as tissue adhesives, endovascular paving, formation of barriers to prevent post-surgical adhesions, or any application involving the "adhesion" of the matrix to one or more surfaces. Since initiators exhibiting this type of reactivity can abstract hydrogens from adjacent molecules, when a macromer system containing polymeric initiators of this type is applied to a substrate, photoactivation of the system causes the abstraction of hydrogens from the substrate by the initiators, thus forming a free radical on the substrate and a free radical on the initiator. This diradical can subsequently collapse forming a covalent bond between the macromer system and the substrate.

Other initiator groups on the same macromer initiate free radical reactions with other macromers resulting in the formation of a crosslinked matrix covalently bound to the surface. Initiator groups exhibiting this type of reactivity include analogs of benzophenone and thioxanthone.

Optionally, the use of initiators for initiating the necessary radical chain polymerization, can include the addition of one or more monomeric polymerization accelerants to the polymerization mixture, the accelerants serving to enhance the efficiency of polymerization. Polymerization accelerants useful in the present invention are typically monomers, which improve the reactivity of the macromer systems. Polymerization accelerants that have found particular utility for this application are N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the macromer system.

In another embodiment, the polymeric initiator comprises a polymeric backbone with pendent initiator groups and pendent reactive or affinity groups. These reactive or affinity groups enable the polymeric initiator to bind to target groups on surfaces of interest. This allows the polymeric initiator to bind to the surface of interest. In this manner, interfacial polymerization of macromers can be accomplished. A solution of polymeric initiator-containing pendent reactive or affinity groups is applied to a surface with target sites. The reactive or affinity groups on the polymeric initiator react with the sites on the surface causing the polymeric initiator to bind to the surface. Excess polymeric initiator can then be washed away. A solution of a polymerizable macromer is then applied to the surface. When light energy in applied to the system, a free radical polymerization reaction is initiated only at the surface of interest. By varying the concentration of the polymerizable macromer and the illumination time, the thickness and crosslink density of the resulting matrix on the surface can be manipulated.

In this embodiment, a multifunctional polymeric initiator of the invention is synthesized having a polymeric backbone, one or more photoreactive moieties, and two or more bioactive groups. The polymeric initiator may be brought into contact with the surface of a previously formed biomaterial or into contact with another polymeric molecule. The photoreactive moieties are energized via an external stimulation to form active specie generation, which in turn causes polymerization of the macromer system.

The polymer backbone of the multifunctional polymeric initiator can be either synthetic or naturally occurring, and is preferably a synthetic polymer selected from the group consisting of oligomers, homopolymers, and copolymers resulting from addition or condensation polymerization. Naturally occurring polymers, such as polysaccharides and polypeptides, can be used as well. Preferred backbones are biologically inert, in that they do not provide a biological function that is inconsistent with, or detrimental to, their use in the manner described.

Such polymer backbones can include acrylics such as those polymerized from hydroxyethyl acrylate, hydroxyethyl methacrylate, glyceryl acrylate, glyceryl methacrylate, acrylic acid, methacrylic acid, acrylamide and methacrylamide; vinyls such as polyvinyl pyrrolidone and polyvinyl alcohol; nylons such as polycaprolactam, polylauryl lactam, polyhexamethylene adipamide and polyhexamethylene dodecanediamide; polyurethanes; polyethers such as polyethylene oxide, polypropylene oxide, and polybutylene oxide; and biodegradable polymers such as polylactic acid, polyglycolic acid, polydioxanone, polyanhydrides, and polyorthoesters.

The polymeric backbone is chosen to provide a backbone capable of bearing one or more photoreactive moieties and two or more bioactive groups. The polymeric backbone is also selected to provide a spacer between the surface and the various photoreactive moieties and bioactive groups. In this manner, the reagent can be bonded to a surface or to an adjacent reagent molecule, to provide the bioactive groups with sufficient freedom of movement to demonstrate optimal activity. The polymer backbones are preferably water soluble, with polyacrylamide and polyvinylpyrrolidone being particularly preferred polymers.

Multifunctional reagents in this initiator system carry one or more pendent latent reactive (preferably photoreactive) moieties covalently bonded to the polymer backbone. Photoreactive moieties are defined herein, and preferred moieties are sufficiently stable to be stored under conditions in which they retain such properties.

Photoreactive moieties respond to specific applied external stimuli to undergo active specie generation with resultant covalent boding to an adjacent chemical structure, e.g., as provided by the same or a different molecule. Photoreactive moieties are those groups of atoms in a molecule that retain their covalent bonds unchanged under conditions of storage but that, upon activation by an external energy source, form covalent bonds with other molecules and can cause polymerization of macromer systems.

Low molecular weight bioactive groups are typically those that are intended to enhance or alter the function or performance of a particular biomedical device in a physiological environment, and such bioactive groups may be included on polymeric backbone with the initiator group. In a particularly preferred embodiment, the bioactive group is selected from the group consisting of cell attachment factors, growth factors, antithrombotic factors, binding receptors, ligands, enzymes, antibiotics, and nucleic acids. Desirable antithrombotic agents include heparin and hirudin (which inhibit clotting cascade proteins such as thrombin) as well as lysine. Other desirable antithrombotic agents include prostaglandins such as PGI2, PGE1, and PGD2, which inhibit platelet adhesion and activation. Still other desirable antithrombotic agents include fibrinolytic enzymes such as streptokinase, urokinase, and plasminogen activator, which degrade fibrin clots. Another desirable bioactive group consists of lysine, which binds specifically to plasminogen, which in turn degrades fibrin clots. An initiator group of this embodiment includes at least one pendent bioactive group. The use of two or more pendent bioactive groups is presently preferred, however, since the presence of several such groups per initiator group tends to facilitate the use of such initiator systems.

Other desirable bioactive groups present in this initiator group include growth factors, such as fibroblastic growth factors, epidermal growth factor, platelet-derived growth factors, transforming growth factors, vascular endothelial growth factor, bone morphogenic proteins and other bone growth factors, neural growth factors, and the like.

Generally, there are two methods by which an initiator group can be incorporated into a polymeric backbone. The first method involves the formation of a monomer which includes the initiator. This can be accomplished readily using standard chemical reactions. For example, the acid chloride analog of an initiator can be reacted with an amine-containing monomer, to form a monomer which contains the initiator.

The second method of incorporating initiator groups into a polymeric backbone involves coupling a reactive analog of the initiator with a preformed polymer. For example, an acid chloride analog of an initiator can be reacted with a polymer containing pendent amine groups forming a polymer bearing pendent initiator groups.

Macromer systems can be applied to a tissue site and/or implant article in any suitable manner, including by spraying, dipping, injecting or brushing the macromer system. Polymeric matrices prepared from macromer systems can be used in a variety of applications, including:

Cellular Encapsulation. The use of hydrogels to form micro- or macrocapsules containing cells and other tissue, is well documented in the literature. Applications include the treatment of diabetes, Parkinson's disease, Alzheimer's disease, ALS, chronic pain, and others. Descriptions of cellular encapsulation methods can be found throughout the patent and scientific literature. The use of the instant invention provides methods of encapsulating cells in two basic ways.

1) Bulk Polymerization

In this embodiment, cellular material is mixed in a solution of the macromer system and energy subsequently added to activate initiation of free radical polymerization. Prior to initiation, the solution containing the macromer system with suspended cellular material, can be placed in molds, shaped in particular geometric shapes, or placed inside a preformed membrane system, such as a hollow fiber. Upon illumination or other energy addition, the initiation of free radical polymerization causes the macromer system to gel, forming a cell-containing matrix in the desired shape. When formed into free-standing geometric shapes, the formulation of the macromer system can be designed to provide the desired degrees of durability and permselectivity to the subsequently formed matrix. When formed inside membrane structures, such as hollow fibers designed to provide the desired permselectivity, the macromer system can be formulated to provide the desired characteristics of the cell-suspending matrix, such as biocompatibility, etc.

2) Interfacial Polymerization

In this embodiment, a membrane is formed directly on the surface of the cellular material. A solution of polymerizable or non-polymerizable polymeric initiator-containing pendent affinity groups (e.g., positively charged groups) is mixed with the cellular material. The affinity groups bind to the sites on the surface of the cellular material. The excess polymeric initiator is subsequently washed away and the cellular material suspended in a solution of polymerizable macromer. Since initiator groups are present only at the surface of the cellular material, when light energy is applied, polymerization is initiated only at the surface: macromer interface. By manipulating the duration of illumination and macromer formulation, a polymeric matrix exhibiting the desired characteristics of thickness, durability, permselectivity, etc. is formed directly on the surface of the cellular material.

Adhesives and sealants. Polymeric matrix systems have also found extensive use as adhesives for tissue and other surfaces. For this application, a solution of a macromer system is applied to a surface to which adhesion is desired, another surface is contacted with this surface, and illumination is applied forming a surface-to-surface junction. If a temporary adhesive is desired, the macromer system can be composed of degradable macromers.

Barriers. Polymeric matrices can be used for the formation of barriers on surfaces for various applications. One such application is a barrier for the prevention of tissue adhesions following surgery. For this application, a macromer system in liquid form is applied to the surface of damaged tissue. The liquid is illuminated to polymerize the macromers. The polymeric matrix prevents other tissue from adhering to the damaged tissue. Both degradable and non-degradable macromer systems can be used for this purpose. As described above, both bulk polymerization and interfacial polymerization methods can be used to prepare surface coatings of this type.

Hemocompatiblity. Polymeric matrices can be used to form hemocompatible surfaces for various applications. An exemplary application is a surface on a device or tissue that provides hemocompatiblity during the healing process. For this application, a multifunctional polymerization initiator system comprising photoreactive molecules and hemocompatible molecules, e.g. fatty acids or lysine, is applied to a surface and crosslinked. Desirable proteins, e.g. serum albumin, are attracted to this surface and stimulate the healing process. Such a surface discourages the absorbance of undesirable proteins, e.g. fibrinogen, which inhibit the heaping process.

Controlled Release Carriers. Polymeric matrices find wide application as controlled release vehicles. For this application, a solution of a macromer system and drug, protein, or other active substance is applied to a surface. The solution is illuminated to polymerize the macromers. The polymeric matrix contains the drug, when exposed to a physiological or other liquid-containing environment, the drug is slowly released into the environment. The release profile of the entrained drug can be manipulated by varying the formulation of the macromer system. Both degradable and non-degradable macromer systems can be utilized for this purpose. Likewise, both bulk and interfacial polymerization techniques can be used to prepare controlled drug-releasing surfaces. In an alternative embodiment, a drug or other active substance can be imbibed by a preformed matrix on a surface. The absorption and release characteristics of the matrix can be manipulated by varying the crosslink density, the hydrophobicity of the matrix, and the solvent used for imbibition.

Alternatively, drug-containing polymeric microspheres can be prepared using standard techniques. A wide range of drugs and bioactive materials can be delivered using the invention which include but are not limited to, antithrombogenic, anti-inflammatory, antimicrobial, antiproliferative, and anticancer agents, as well as growth factors, morphogenic proteins, and the like.

Tissue Replacement/Scaffolding. Polymeric matrices have found utility as three-dimensional scaffolding for hybrid tissues and organs. For this application, a macromer system in liquid form is applied to a tissue defect and subsequently illuminated to polymerize the macromers forming a matrix upon which ingrowing cells can migrate and organize into a functional tissue. In one embodiment, the macromer system additionally includes a growth factor which is slowly released and stimulates the ingrowth of desired cell types. In another embodiment, the macromers include pendent extracellular matrix peptides which can stimulate the ingrowth of desired cell types. A third embodiment would include both of the above features. An alternative embodiment includes cells included in the matrix with or without additional growth factor. The scaffolding can be generated in vitro by placing the liquid macromer system in a mold or cavities in a device, or can be generated in vivo by applying the liquid macromer system to a tissue defect. Both degradable and non-degradable macromer systems could be used for this application, but degradable matrices are preferred.

Wound Dressing. Polymeric matrices have been used extensively as superior wound dressing preparations. Currently, hydrogel and hydrocolloid wound dressing materials are being increasingly used due to their superior wound healing properties. For this application, a macromer system in liquid form is applied to the wound site and subsequently formed into a flexible polymeric matrix upon exposure to light. When applied as a liquid, the macromer preparation conforms to the irregular surface of the wound. Upon illumination, a flexible matrix is formed which is completely conformal to the surface of the wound; no fluid-filled pockets which can act as sites of bacterial infiltration can exist. In one embodiment, the macromer system additionally includes one or more therapeutic agents, such as growth factors or antimicrobial agents which are slowly released into the wound. Both degradable and non-degradable macromer systems can be used for this application.

In Situ Device Formation. Polymeric materials can be implanted into the body to replace or support the function of diseased or damaged tissues. One example of this is the use of hollow cylindrical polymeric devices to support the structure of a coronary artery following percutaneous transluminal coronary angioplasty (PTCA). Currently, pre-formed cylindrical devices are implanted via catheter insertion followed by balloon expansion to secure the device. The expanded device supports the structure of the artery and prevents the reversion of the artery to the closed position (restenosis).

For this application, a liquid macromer preparation could be applied to an injured artery via a multi-lumen catheter containing an illumination element. After application of the liquid macromer system to the injured tissue, a semi-rigid polymeric matrix can be formed by a brief illumination. Upon removal of the catheter, a hollow, cylindrical, conformal polymeric device remains to support the artery and prevent restenosis. In one embodiment, the macromer system additionally includes a releasable therapeutic agent or agents, such as antiproliferative and/or antithrombotic drugs. These agents are slowly released from the formed matrix, to provide additional therapeutic benefit to the injured tissues. Both degradable and non-degradable macromer systems can be used for this application.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight

EXAMPLES

Example 1

Synthesis of
7-Methyl-9-oxothioxanthene-3-carboxylic Acid
Chloride (MTA-Cl)

The 7-methyl-9-oxothioxanthene-3-carboxylic acid (MTA), 50.0 g (0.185 mol), was dissolved in 350 ml of toluene and 415 ml (5.69 mol) of thionyl chloride using an overhead stirrer in a 2 liter 3-neck round bottom flask. N,N-Dimethylformamide (DMF), 2 ml, was added and the reaction was brought to reflux for 2 hours. After this time, the mixture was stirred at room temperature for 16 hours. The solvent was removed under vacuum and the product was azeotroped with 3×350 ml of toluene to remove the excess thionyl chloride. The product was recrystallized from 800 ml of chloroform and the resulting solid was placed in a vacuum oven for 16 hours at 45° C. to complete removal of solvent. The isolated product weighed 45.31 g (85% yield) and nuclear magnetic resonance spectroscopy (NMR) confirmed the desired structure. This product was used for the preparation of a photoreactive monomer as described in Example 2.

Example 2

Synthesis of N-[3-(7-Methyl-9-oxothioxanthene-3 -carboxamido)propyl]methacrylamide (MTA-APMA)

The N-(3-aminopropyl)methacrylamide hydrochloride (APMA), 4.53 g (25.4 mmol), was suspended in 100 ml of anhydrous chloroform in a 250 ml round bottom flask equipped with a drying tube. After cooling the slurry in an ice bath, the MTA-CL, 7.69 g (26.6 mmol), was added as a solid with stirring. A solution of 7.42 ml (53.2 mmol) of triethylamine (TEA) in 20 ml of chloroform was then added over a 1.5 hour time period, followed by a slow warming to room temperature. The mixture was allowed to stir 16 hours at room temperature under a drying tube. After this time, the reaction was washed with 0.1 N HCl and the solvent was removed under vacuum after adding a small amount of phenothiazine as an inhibitor. The resulting product was recrystallized from tetrahydrofuran (THF)/toluene (3/1) and gave 8.87 g (88.7% yield) of product after air drying. The structure of the compound was confirmed by NMR analysis.

Example 3

Preparation of N-Succinimidyl 6-Maleimidohexanoate (MAL-EAC-NOS)

6-Aminohexanoic acid, 100.0 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-aza-2-undecendioic acid was 158-165 g (90-95%) with a melting point of 160-165° C. Analysis on an NMR spectrometer was consistent with the desired product.

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a Celite 545 pad to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from hexane/chloroform (2/1) to give typical yields of 76-83 g (55-60%) with a melting point of 81-85° C. Analysis on a NMR spectrometer was consistent with the desired product.

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12.0 g (0.104 mol) of N-hydroxysuccinimide and 16.0 ml (0.114 mol) of triethylamine. After stirring overnight at room temperature, the product was washed with 4×100 ml of water and dried over sodium sulfate. Removal of solvent gave 24.0 g (82%) of MAL-EAC-NOS which was used without further purification. Analysis on an NMR spectrometer was consistent with the desired product.

Example 4

Preparation of a Copolymer of MTA-APMA, MAL-EAC-NOS, and N-Vinylpyrrolidone

A polymeric initiator is prepared by copolymerization of a monomer charge consisting of 5 mole % MTA-APMA, 10 mole % MAL-EAC-NOS, and 85 mole % N-vinylpyrrolidone (VP). The polymerization is run in formamide or other suitable solvent using 2,2'-azobisisobutyronitrile (AIBN) as an initiator and N,N,N',N'-tetramethylethylenediamine (TEMED) as an oxygen scavenger. Mercaptoethanol is added as a chain transfer reagent at a concentration designed to give a molecular weight between 2,000 and 20,000 daltons. Upon completion of the polymerization, the copolymer is precipitated by addition of ether or other non-solvent for the polymer. After isolation by filtration, the product is washed extensively with the precipitating solvent to remove residual monomers and low molecular weight oligomers. The copolymer is dried under vacuum and is stored desiccated to protect the hydrolyzable N-oxysuccinimide (NOS) esters.

Example 5

Synthesis of a Photoreactive Macromer Derived from a Poly(caprolactone-co-lactide) Derivative of Pentaerythritol Ethoxylate A 15 gram scale reaction was performed by charging a thick-walled tube with 8.147 g (56.5 mmol) of 1-lactide (3,6-dimethyl-1,4-dioxane-2,5-dione) and 6.450 g (56.5 mmol) of ε-caprolactone. To this mixture was added 0.402 g (1.49 mmol) of pentaerythritol ethoxylate (ave. MW appprox. 270) to provide polymerization sites and control molecular weight. This mixture was warmed gently until dissolution of all reagents was complete. The catalyst, stannous 2-ethylhexanoate (0.015 ml) was added and the reaction vessel sealed. The reaction mixture was warmed to 150° C. and stirred for 20 hours. The resulting polymer was dissolved in chloroform and dialyzed against methanol using 1000 MWCO dialysis tubing. After dialysis, the solvent was removed in vacuo. The purified polymer was dissolved in chloroform and treated with 2.41 g (23.8 mmol) of TEA. To this reaction mixture was added 292 mg (1.19 mmol) of 4-benzoylbenzoyl chloride (BBA-Cl) and the resulting mixture was stirred for 16 hours. To this reaction mixture was added 0.734 g (8.11 mmol) of acryloyl chloride and the reaction was stirred an additional 8 hours. The modified polymer was purified by dialysis against methanol using 1000 MWCO dialysis tubing. After dialysis, the solvent was removed in vacuo and the polymer (15.36 grams) stored desiccated at room temperature.

Example 6

Synthesis of Water Soluble Siloxane Macromer with Pendent Initiator Groups

Fifty grams of a water-soluble siloxane macromer with pendent initiator groups were synthesized by first dissolving 50 grams of commercially available poly[dimethylsiloxane-co-methyl (3-hydroxypropyl)siloxane]-graft-poly(ethylene glycol) 3-aminopropyl ether (Aldrich Chemical) in 50 ml of methylene chloride. To this solution was added 5.0 g (49 mmol) of TEA. The reaction solution was cooled to −50° C., then transferred to a stir plate at room temperature. MTA-Cl, 1.0 g (3.5 mmol), prepared according to the general method in Example 1, and 5.0 g (55 mmol) of acryloyl chloride were added and the solution was stirred for 6 hours at room temperature. The solution was dialyzed against deionized water using 3500 MWCO dialysis tubing and the water was subsequently removed in vacuo. The product (48.4 grams) was stored desiccated at room temperature.

Example 7

Synthesis of a Polymerizable Hyaluronic Acid

Two grams of hyaluronic acid (Lifecore Biomedical, Chaska, Minn.) were dissolved in 100 ml of dry formamide. To this solution were added 1.0 g (9.9 mmol) of TEA and 4.0 g (31 mmol) of glycidyl acrylate. The reaction mixture was stirred at 37° C. for 72 hours. After exhaustive dialysis against deionized water using 12-14 k MWCO dialysis tubing, the product (2.89 grams) was isolated by lyophilization.

Example 8

Preparation of a Photoderivatized Polyacrylamide (Photo-PAA)

Acrylamide, 10.24 g (0.144 mol), was dissolved in 200 ml of deionized water. To the solution was added 0.279 g (1.56 mmol) of APMA, 0.33 g (1.45 mmol) of ammonium persulfate and 0.155 g (1.33 mmol) of TEMED. The solution was evacuated in a filter flask with a water aspirator for 10 minutes. The tubing was clamped and the solution left under vacuum for one hour. The resulting polymer solution was dialyzed against deionized water using 12-14 k MWCO dialysis tubing. To 150 ml of polymer solution in a PTFE bottle containing 3.0 grams of polymer was added 0.504 ml (3.62 mmol) of TEA. To this solution was added 30 ml of 28.4 mg/ml (3.48 mmol) 4-benzoylbenzoyl chloride in $CHCl_3$. The bottle was capped tightly and shaken for one hour. The bottle was then centrifuged for 10 minutes to separate the phases after which the aqueous layer was removed, dialyzed against deinoized water using 12-14 k MWCO dialysis tubing, and lyophilized. The product (3.21 grams) was stored, dessicated at room temperature.

Example 9

Synthesis of the N-Hydroxysuccinimide Ester of Eosin Y

Eosin Y, 1.00 g (1.54 mmol), was dissolved in 10 ml dry dioxane with stirring, gentle warming and some sonication. After the solution was complete, the orange solution was cooled to room temperature under argon. N-Hydroxysuccinimide, 0.195 g (1.69 mmol), and 1,3-dicyclohexylcarbodiimide, 0.635 g (3.08 mmol), were added as solids. The resulting red mixture was stirred at room temperature for 48 hours under an inert atmosphere. After this time the solid was removed by filtration and washed with dioxane. The filtrate was concentrated in vacuo to give 1.08 g (94% yield) of a glassy red solid.

Example 10

Synthesis of a Copolymer of APMA, Methyl Methacrylate, and N-Vinylpyrrolidone Followed by Addition of Acryloyl Groups The following ingredients for the copolymer were placed in a glass vessel and dissolved in 20 ml DMSO: APMA (2.68 g, 15.0 mmol), VP (6.74 ml, 63.1 mmol), methyl methacrylate (mMA) (0.334 ml, 3.12 mmol), mercaptoethanol (0.053 ml, 0.76 mmol), AIBN (0.041 g, 0.25 mmol), and TEMED (0.057 ml, 0.38 mmol). After solution was complete, the monomer solution was degassed, blanketed with argon and placed in an agitating incubator at 55° C. The copolymer was dialyzed against deionized water in 6-8,000 MWCO dialysis tubing. The dialyzed solution (~400 ml) was loaded with acrylate groups. TEA, 5.0 ml (35.9 mmol), was added with stirring. The solution was placed in a freezer for 5-10 minutes to cool. After this time, 5.0 ml (61.5 mmol) of acryloyl chloride in 5 ml of chloroform were added with stirring. The reaction mixture was stirred at room temperature for 16 hrs. After this time the acrylated polymer was dialyzed against deionized water using 6-8,000 MWCO tubing. The product was lyophilized and 7.10 g were obtained.

Example 11

Synthesis of a Copolymer of MTA-APMA, APMA, Methyl Methacrylate, and N-Vinylpyrrolidone Followed by Addition of Acryloyl Groups The following ingredients for the copolymer were placed in a glass vessel and dissolved in 20 ml DMSO: MTA-APMA (0.613 g, 1.55 mmol), APMA (2.578 g, 14.4 mmol), VP (6.27 ml, 58.7 mmol), mMA (0.319 ml, 2.98 mmol), mercaptoethanol (0.054 ml, 0.77 mmol), AIBN (0.039 g, 0.24 mmol), and TEMED (0.053 ml, 0.35 mmol). After solution was complete, the monomer solution was degassed, blanketed with argon and placed in an agitating incubator at 55° C. The copolymer was dialyzed against deionized water in 6-8,000 MWCO dialysis tubing. The dialyzed solution was protected from light and loaded with acrylate groups. TEA, 5.0 ml (35.9 mmol), was added with stirring. The solution was placed in a freezer for 5-10 minutes to cool. After this time, 5.0 ml (61.5 mmol) of acryloyl chloride in 5 ml of chloroform were added with stirring. The reaction mixture was stirred at room temperature for 9 hrs. After this time the acrylated polymer was dialyzed against deionized water using 6-8,000 MWCO tubing and protected from light. The product (8.88 grams) was isolated by lyophilization.

Example 12

Evaluation of Matrix Formation

A 15% solution of the co-polymer from Example 11 was prepared in 10% DMS0/water. The MTA content of the solution was estimated by measuring the absorbance of the solution at 395 nm (A@395 nm=42.6). A 15% solution of the co-polymer from Example 10 (same co-polymer as that described in Example 11 but with no MTA-APMA) was prepared in 10% DMSO/water. MTA was added to this solution until its absorbance at 395 nm matched that of the solution described above. The two solutions were identical in concentration of co-polymer and photoinitiator, the only difference between them being that in one solution the photoinitiator was present in polymeric form (POLY) and in the other the photoinitiator was present in non-polymeric form (NON).

In order to compare the matrix forming ability of the two solutions the following evaluation was undertaken: the indentations in the lid of a 96 well microtiter plate were used as miniature molds to evaluate the ability of the photoreactive polymer solutions to form solid hydrogel discs upon illumination. The indentations are eight millimeters in diameter and approximately 0.6 millimeters deep. 30 microliters of polymer solution will just fill the indentation. Thirty microliters of both the (POLY) and (NON) solutions were added to wells. After addition of the polymer solutions, the lids were illuminated using an EFOS Ultracure 100 SS illumination system equipped with a 400-500 nm filter, for varying lengths of time. After illumination the lid was flooded with water and each polymer formulation rated for its ability to form solid discs using the following arbitrary scale:

0=liquid, no gelation
1=soft gel, unable to remove from mold
2=firm gel, removable from mold with slight difficulty
3=very firm gel, easily removed from mold
4=very firm gel, elastomeric properties evident Results:

| Polymer | Matrix formation Time (sec) | | | | | |
|---------|---|---|---|---|---|---|
|         | 2 | 5 | 10 | 30 | 60 | 120 |
| (POLY)  | 1 | 2 | 3 | 4 | 4 | 4 |
| (NON)   | 0 | 0 | 1 | 2 | 3 | 3 |

The polymer solution containing the polymer-bound initiator (POLY) formed matrices more rapidly and more completely than the polymer solution containing non-polymer-bound initiator (NON) when exposed to light energy.

Example 13

Synthesis of an Eosin Substituted Polymer

N-Vinylpyrrolidone, 10.0 g (90.0 mmol), was dissolved in 50 ml DMSO. To the solution was added 0.30 g (1.68 mmol) of APMA, 0.15 g (0.91 mmol) of AIBN, and 0.10 g (0.86 mmol) of TEMED. The solution was sparged with nitrogen for 20 minutes and incubated at 55° C. for 20 hours. The resulting polymer was purified by dialysis against water and isolated by lyophiliaztion.

Three grams of the polymer were dissolved in 150 mls dry dioxane. To this solution was added 0.504 ml (3.62 mmoles) of TEA. Subsequently, 2.74 grams (3.5 mmoles) of the N-hydroxysuccinimide ester of Eosin Y was added and the reaction mixture stirred for two hours at room temperature. The solution was dialyzed against dH$_2$O using 12-14 kda cut-off dialysis tubing and lyophilized to isolate the product. The reaction yielded 3.96 grams of red polymer.

Example 14

A Biodegradable Tissue Adhesive

A solution was prepared consisting of 5% polymerizable hyaluronic acid (Example 7) and 2% photoderivatized polyacrylamide (Example 8) in water. This reagent was evaluated for use as a tissue adhesive using cellulose dialysis tubing as a tissue model.

Shear strength testing was performed on dialysis tubing. The tubing was slit and cut into 2 cm×4 cm pieces. The pieces were soaked in water briefly, removed, and tested while still damp. One piece was laid flat on a surface and 10 µl of adhesive applied to one end of the strip. Another piece was laid over this piece with a 1 cm overlap between pieces. When evaluating the photoactivatable adhesive (2/5 HA), the overlap area was illuminated for 10 seconds. When evaluating a control adhesive, the adhesive was allowed to set for five minutes. The bonded samples were mounted in a tensiometer lengthwise by the ends such that the plane of the area of adhesive was parallel to the axis of the tensiometer. The samples were extended at the rate of 1 cm/minute until adhesive or substrate failure, and the force at failure recorded. Substrate-only, and, for photoactivatable adhesive, non-illuminated samples, were included as controls in the evaluations.

| Adhesive | Maximum Force Generated Kg | Adhesive Failed Before Substrate | Substrate Failed Before Adhesive |
|----------|---------------------------|----------------------------------|----------------------------------|
| 2/5 HA   | 0.53  | 0/4 | 4/4 |
| 2/5 HA (no illumination) | 0.081 | 4/4 | 0/4 |
| Fibrin glue | 0.045 | 4/4 | 0/4 |
| Cyanoacrylate | 0.49 | 0/4 | 4/4 |

Example 15

Formation of an In Situ Hydrogel Wound Dressing

Photopolymerizable, matrix-forming reagents were evaluated for efficacy as in situ wound dressings.

Preparation of reagents:

An experimental in situ forming wound dressing was prepared by:

1) Dissolving reactive macromer from Example 10 at 20% into a sterile 6% glycerin solution in water.

2) Preparing a sterile solution of polymeric eosin reagent from Example 12 at 4% in water and a sterile solution of 2M triethanolamine (TEA) in water.

3) Transporting the three sterile solutions to a surgical suite for application to wound sites created on porcine skin.

Four young female China White swine weighing between 15-20 kg were anesthetized and 12 wounds inflicted on one side of each pig. Wounds were 1"×2" and 0.015" deep and were inflicted by a calibrated electrodermatome (Padgett). The wounds were inflicted in two rows of six on the thoracic and paravertebral area of each pig, leaving approximately two inches between adjacent wounds. The wounds were randomized and received one of three treatments:

1) No treatment (control)
2) Application of OpSite®, a semi-occlusive wound dressing from Smith and Nephew, Inc.
3) Experimental photo-curable dressing To apply the experimental dressing, 0.5 mls of the polymeric-eosin solution and 0.5 mls of the TEA solution were added to the macromer/glycerin solution yielding a photo-wound dressing solution. The solution was transferred to 16 three ml sterile syringes (2 ml/syringe) and one syringe was used to application to each wound site. The solutions were applied to each assigned wound site (approximately 1.5 mls solutions/site) and allowed to flow over the site. The solutions were fixed by illumination with a 150 W incandescent light bulb positioned four inches from the wound surface for 30 seconds. The dressing solution readily formed into a durable, rubbery hydrogel which adhered very well to the wound sites. Sterile 4×4 gauze pads were placed over the entire wounded area of each pig, and the pigs placed in sterile stockinettes. On selected days (3, 4, 5, and 7), one pig was euthanized and the effect of dressing on wound epithelialization and repair evaluated.

Evaluation of Effect of Dressing on Wound Epithelialization and Repair:

Following euthanasia, skin wounds were removed from the underlying deep subcutaneous tissue and fixed in 10% neutral buffered formalin solution. After fixation, five biopsy sites from each wound were obtained with a 6 mm Keys skin biopsy punch. Each biopsy was packaged, labeled and submitted for histological sectioning. Histological sections were sectioned at 4 microns and stained with hematoxylin and eosin. Histological sections were examined with the microscope without knowing the type of covering placed over the wound site. The following criteria were evaluated and scored in microscopic examination:

Degree of epithelialization of the wound
Magnitude of the inflammatory reaction
Degree of fibroplasia in the wound
Degree of Damage to Subcutaneous Tissue:

Morphometric analysis of cell types in the histological sections were used to help differentiate the degree of inflammatory reaction present. The number of polymorphonuclear cells, lymphocytic cells, and fibroblasts was evaluated. Each histological biopsy was graded on a scale of 1-5.

Degree of Inflammatory Reaction:
1. No or borderline cellular inflammatory reaction
2. Minimal inflammation
3. Moderate density of inflammatory cells with some exudate
4. Severe, high density of inflammatory cells in or on the wound tissue with thicker layer of exudate
5. Excessive inflammation, with signs of dense foci of inflammatory cells infiltrating the wound tissue or on the wound and forming a thick layer of inflammatory exudate.

Degree of Wound Epithelialization:
1. Stratum corneum present at least 4 layers of cells and entire epidermal surface is present.
2. Stratum corneum is present at least 1 layer of cells and entire epidermal surface is present.
3. Stratum corneum is present at least 1 layer of cells and ½ of epidermal surface is covered.
4. No stratum corneum is present; minimal inflammation of the subepidermal tissue.
5. No stratum corneum is present; moderate inflammation in subepidermal tissue.

Degree of Fibroplasia in the Wound:
1. No fibroplasia in the wound
2. Mild fibroplasia in the wound involving ⅓ to ½ wound surface
3. Mild fibroplasia in the wound involving ⅔ or more of the wound
4. Moderate fibroplasia involving ⅓ to ½ of the wound
5. Severe fibroplasia involving ½ or more of the wound Degree of Damage to the Subcutaneous Tissue:
1. No damage to the subcutaneous tissue
2. Mild damage to the subcutaneous tissue with mild edema and few inflammatory cells.
3. Moderate damage to the subcutaneous tissue with moderate edema and moderate accumulation of inflammatory cells
4. Severe damage to the subcutaneous tissue with severe edema and large number of inflammatory cells
5. Excessive damage to the subcutaneous tissue with dense foci of inflammatory cells Results:

Each biopsy was graded blindly using the criteria listed above. When the histological examination was completed, the graded biopsies were correlated with the wound sites. A single average score for each dressing was calculated by adding all the scores for every site for each dressing and dividing by the number or scores.

The total scores for each type of wound dressing on days 3, 4, 5, and 7 were evaluated with an ANOVA SAS program for data intervals to statistically evaluate if there was any difference between the three types of wound treatments administered. Only two scores were found to be statistically significant:
1. On day 4 following wound creation the mean for the OpSite® dressing was 2.4 and was found to be statistically significant when compared to the control and experimental wound sites.
2. On day 7 following the creation of the wounds the mean for the experimental dressing, 1.8 was found to be statistically significant when compared to the control and the OpSite® wound dressings.

On day 7 post-wound creation, the wound sites treated with the experimental photocurable dressing showed significantly superior healing to those that were untreated or treated with OpSite® dressing, as judged by the criteria described.

Example 16

A Bioresorbable Drug Delivery Coating

A solution of 33% of the macromer from Example 5 was prepared in ethanol. Ten centimeter lengths of polyurethane rod (PU) were dipped into the macromer solutions and illuminated for six minutes to form a matrix. This procedure resulted in the formation of a very durable, tenacious, and flexible coating on the rod. One gram of chlorhexidine diacetate (an antimicrobial agent) was dissolved in 10 mls of the macromer solution and the coating process repeated on additional PU rods. This also resulted in a tenacious, durable, and flexible coating on the rods. The rods were cut into one centimeter pieces and evaluated in a zone of inhibition analysis.

Coated dye-containing pieces, coated no-drug controls, and uncoated pieces were placed in Mueller-Hinton agar plates which were swabbed with a $10^6$ suspension of Staphylococcus epidermidis (Christensen RP62A). These pieces functioned as unwashed controls and were transferred to freshly swabbed agar plates each day for 60 days.

Additional pieces, no-drug controls (both coated and uncoated) and drug-incorporated coated, were placed in snap-cap vials and washed with 50% Normal Calf Serum in PBS. The tubes were placed on an orbital shaker and incubated at 37° C. and 200 rpm for 20 days. Each day the wash solution was removed and replaced with fresh solution. Periodically, pieces were removed from the serum/PBS and placed in agar as described above. Zones of inhibition resulting from these pieces were recorded and compared to the zones produced by unwashed pieces.

The no-drug coated control pieces, both coated and uncoated, produced no zones. On day 0, both washed and unwashed drug-incorporated pieces produced zone of 24.5 mm. On day 20, when the final washed pieces were evaluated, the unwashed pieces were producing zones of 17.5 mm, and the washed pieces were producing zones of 9.5 mm. On day 60, when the experiment was terminated, the unwashed pieces were still producing zones of 17 mm.

This experiment demonstrates the utility of this matrix-forming polymer at producing drug delivery coatings which provide a long-term delivery of a bioactive agent.

Example 17

A Biostable Drug Delivery Coating

A solution of 25% of the macromer from Example 6 was prepared in 50% IPA/H$_2$O. Ten centimeter lengths of polyurethane rod were dipped into the macromer solution and illuminated for six minutes to form matrix. This procedure resulted in the formation of a very durable, tenacious, and flexible coating on the rod. Five hundred milligrams of chlorhexidine diacetate was dissolved in 10 mls ethanol. Half of the coated rods were soaked in this solution for 60 minutes at room temperature, and half of the rods were soaked in neat ethanol under the same conditions. After soaking, the rods were removed from the ethanol and allowed to dry for 20 hours at room temperature. The rods were cut into one centimeter pieces and evaluated in a zone of inhibition analysis.

Uncoated control, coated control, and coated drug-incorporated pieces were placed in Mueller-Hinton agar plates which were swabbed with a $10^6$ suspension of Staphylococcus epidermidis (Christensen RP62A). These plates were incubated for 20 hours at 37° C. The zone where no bacterial growth was evident around each piece was measured and the piece transferred to a freshly swabbed agar plate each day for 14 days.

The uncoated control pieces and the coated control pieces produced no zones. On day 0, the drug-incorporated coated pieces produced average zones of 25 mm. These pieces continued to produce zones each day. On day 14, when the experiment was terminated, the pieces produced average zones of 6 mm.

Example 18

Formation of a Three-Dimensional Device

One end of a 3 mm diameter teflon-coated rod was dipped to a level of 1.5 cm in neat BBA-acryloylpolytetra(caprolactone-co-lactide)pentaerythritol ethoxylate (see Example 5) and immediately illuminated, with rotation, for 10 seconds suspended between opposed Dymax lamps. After illumination, a semi-rigid elastomeric coating had formed on the rod. The rod was cooled to facilitate removal of the polymeric coating. The closed end of the cylinder was removed with a razor blade, thus forming a hollow cylindrical device of 1.25 cm in length and 3.5 mm in diameter.

Example 19

Synthesis of a Polymerizable Collagen

One gram of soluble collagen (Semed-S, Kensey-Nash Corp.) (a mixture of Types I and III) was dissolved in 50 mls of 0.01 N HCl. When dissolved, 1.25 gms triethylamine (12.4 mmoles) was added to the reaction mixture. One gram of acryloyl chloride (11.0 mmoles) dissolved in one milliliter of methylene chloride was added to the reaction vessel and the mixture was stirred for 20 hours at room temperature.

The reaction mixture was dialyzed exhaustively against dH$_2$O, and the product isolated by lyophilization. A yield of 1.17 grams of polymerizable collagen was realized.

Example 20

A Collagen Scaffolding that Contains a Bone Morphogenic Protein

A. Preparation of the solidified scaffolding.

A solution of liquid macromer is prepared which consists of 5% (w/v) of polymerizable collagen (Example 19) plus 1% (w/v) of photoderivatized polyacrylamide (prepared as described in Example 8) in phosphate buffered saline, pH 7.4. To this is added 50 µg/ml (0.005% w/v) of bone morphogenic protein (BMP-7 from a private source). Aliquots of the above solution (150 µl) are then placed in molds (8 mm diameter and 3 mm high) and are illuminated for 10 seconds with a Dymax lamp (as described in Example 13) to solidify the collagen scaffolding. Control disks of solidified collagen scaffolding are prepared via the same protocol except that BMP-7 is not added.

B. Evaluation of the Solidified Scaffolding.

Disks of solidified collagen scaffolding with BMP-7 are evaluated for stimulation of bone growth in a rat cranial only implant model. In this model, the periosteal membrane is removed and the collagen disks are implanted on the cranium. After 30 days, the implants and adjacent cranial bone are removed, fixed in cold methanol, embedded in PMMA, sectioned, ground to 50-100 µm thickness, stained with Sandersons Rapid Bone Stain, and counterstained with Van Gieson's picro-fuchsin. This protocol evaluates nondecalcified bone, with mature bone staining red, immature bone staining pink, cartilage staining blue-gray, and undegraded collagen appearing acellular and pale yellow.

One control consists of disks of solidified collagen scaffolding lacking BMP-7. A second control consists of 150 µl of nonilluminated liquid macromer solution which contains BMP-7 (the same solution composition that was placed in molds and illuminated to produce the solidified collagen scaffolding containing BMP-7).

When evaluated histologically at 30 days as described above, the experimental disks (solidified collagen scaffolding containing BMP-7) show extensive bone formation in the space originally occupied by the collagen disk. In contrast, both controls (the solidified collagen scaffolding lacking BMP-7 and the nonilluminated liquid control solution containing BMP-7) show little or no bone formation. The amount of bone that forms with the controls is less than 25% of that observed with the experimental disks, therefore demonstrating that the solidified collagen scaffolding greatly enhances BMP-stimulated bone formation.

Example 21

Synthesis of a Polymerizable Collagen

Dissolved 0.5 gram collagen (insoluble bovine tendon collagen, Type I, ReGen Corp.) in 20 mls dry formamide by incubating for 20 hours on an orbital shaker at 37 degrees C. With stirring, added 1.0 gram (9.8 mmol) TEA and equilibrated for 60 minutes in ice water bath. With stirring, added 1.0 gram (11 mmol) acryloyl chloride, in 0.25 gram aliquots (1 aliquot/min). After the final addition, stirred in ice water bath for 2 hours. Removed from ice water bath and continued to stir at room temperature for 18 hours. The product was purified by dialysis against deionized water using 6-8K MWCO dialysis tubing, and isolated by lyophilization.

Example 22

Preparation of a Photoreactive Random Copolymer of Acrylamide and Fatty Acid Monomers Acrylamide, 0.657 g (9.24 mmol), was dissolved in 9 ml of THF, followed by the addition of 0.307 g (0.70 mmol) of N-[3-Methacrylamido)propyl]-2-(carboxymethyl) hexadecanamide and N-[3-Methacrylamido)propyl]-3-carboxyheptadecanamide as made in U.S. Pat. No. 6,465,525, prepared according to the general method described in Example 19 of U.S. Pat. No. 6,465,525, 0.036 g (0.10 mmol) of N-[3-(4-Benzoylbenzamido)propyl]methacrylamide as made in U.S. Pat. No. 6,465,525, prepared according to the general method described in Example 20 of U.S. Pat. No. 6,465,525, 9.0 microliters (0.060 mmol) of TEMED, and 0.026 g (0.16 mmol) of AIBN. The solution was sparged two minutes with helium, two minutes with argon, and was then sealed and heated overnight at 55 degree. C. The resulting suspension was diluted with 5 ml of additional THF and added to diethyl ether, followed by filtration to isolate the solid. After drying in a vacuum oven, 0.997 g of a white solid were isolated. Analysis of the polymer revealed 0.086 mmol of BBA per gram of polymer.

Example 23

Preparation of Trimethylolpropane Ethoxylate (20/3 EO/OH) triacrylate (PEG-triacrylate)

The polyethyleneglycol-triol (PEG-triol; 100.0 g, 98.6 mmoles, Aldrich Chemical Company, Inc., Milwaukee, Wis.) was dissolved with stirring in toluene (200 mLs) and refluxed for one hour. The PEG-triol solution was allowed to cool to approximately 80° C. At this time 4-methoxyphenol (MEHQ; 50 mg, 0.403 mmoles, J. T. Baker, Phillipsburg, N.J.), acrylic acid (42.7 g, 0.592 moles, J. T. Baker, Phillipsburg, N.J.), and sulfuric acid (10 mLs, 0.188 moles, Aldrich Chemical Company, Inc., Milwaukee, Wis.) were added with stirring to the reaction solution. The reaction solution was heated to reflux. The reaction was allowed to progress until about 6.0 mLs of water was produced and collected via a Dean & Stark receiver for approximately one hour. The reaction mixture was allowed to cool to 50° C. and poured into a solution of sodium bicarbonate (270 g in 2.5 liters of deionized water) with stirring. The organic layer was separated, washed with deionized water and dried over sodium sulfate. The PEG-triacrylate was isolated using a wiped film still (Pope Scientific, Inc., Saukville, Wis.).

The structure of the reaction components PEG-triol (a), acrylic acid (b), and the PEG-triacrylate macromer product (c) are shown in the following reaction scheme:

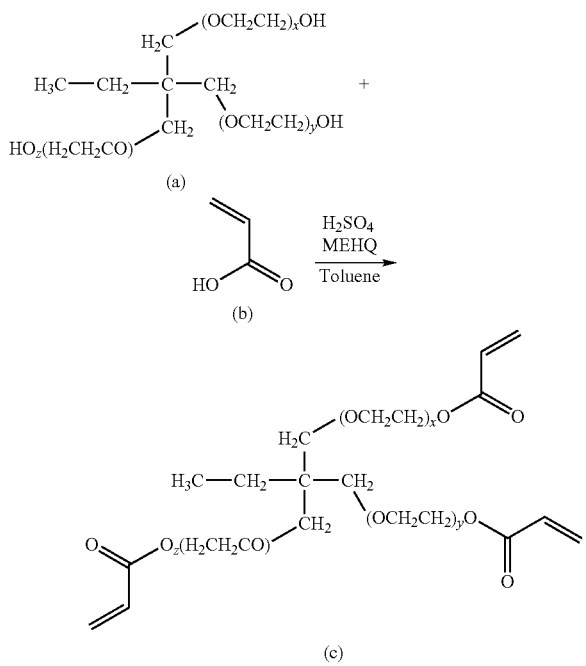

Example 24

PEG Matrix Formation with Photo-Fatty Acid Initiator

Polyurethane and pebax rods were dipped in solutions containing various concentrations of PEG-triacrylate (Example 23) and photo-fatty acid reagent as prepared in Example 22. The dipped rods were illuminated in a UV light Chamber (Goliath) for 3 minutes. After illumination the coated rods were stained with a toluidine blue dye to elucidate the matrix. All coated rods stained evenly with the dye indicating the presence of a PEG matrix on the rods. The coated rods were finger-rubbed and restained. Again, all rods stained evenly, indicating the presence of a durable PEG matrix on the rods.

What is claimed is:

1. A method of reducing immediate and chronic adverse reactions to an implanted medical device, comprising:
   providing a medical device,
   providing a matrix-forming system comprising a multifunctional polymerization initiator and a crosslinkable macromer comprising one or more polymer backbones having pendent polymerizable groups,
   implanting the medical device within a tissue site with the matrix-forming system positioned between the medical device and the tissue, and
   polymerizing the matrix-forming system to form a crosslinked matrix between the medical device and the tissue,
   wherein the multifunctional polymerization initiator is a non-polymer bound initiator and comprises a non-polymeric core with pendent chemical molecules that are capable of initiating a free radical reaction and pendent chemical molecules capable of reducing immediate and chronic adverse reactions to the medical device.

2. The method of claim 1, wherein the backbone comprises polyethylene glycol.

3. The method of claim 1, wherein the polymerizable groups comprise acrylates.

4. The method of claim 1, wherein the chemical molecules that are capable of initiating a free radical reaction are selected from the group consisting of tetrakis (4-benzoylbenzyl ether) of pentaerythritol, 4,5-bis(4-benzoylphenylmethyleneoxy) benzene-1,3-disulfonic acid dipotassium salt (DBDS), and ethylenebis(4-benzoylbenzyldimethylammonium) dibromide (Diphoto-Diquat).

5. The method of claim 1, wherein the chemical molecules that are capable of reducing immediate and chronic adverse reactions to an implanted medical device are selected from the group consisting of fatty acids and salts of organic acids.

6. The method of claim 1, wherein the adverse reactions comprise the adsorbance of undesirable proteins.

7. A coated medical device comprising:
a medical device, and
a matrix-forming system positioned upon the medical device including a multifunctional polymerization initiator and a polymer backbone having pendent polymerizable groups wherein the multifunctional polymerization initiator is a non-polymer bound initiator and comprises a non-polymeric core with pendent chemical molecules that are capable of initiating a free radical reaction and pendent chemical molecules capable of reducing immediate and chronic adverse reactions to the medical device.

8. A method of reducing immediate and chronic adverse reactions to an implanted medical device, comprising:
providing an implantable medical device with a surface having sufficient porosity to permit tissue growth in vivo,
providing a matrix-forming system comprising a multifunctional polymerization initiator and a crosslinikable macromer comprising one or more polymer backbones having pendent polymerizable groups,
implanting the medical device within a tissue site with the matrix-forming system positioned between the medical device and the tissue, and
polymerizing the matrix-forming system to form a crosslinked matrix between the medical device and the tissue,
wherein the multifunctional polymerization initiator is a polymer bound initiator that comprises a polymeric core with pendent chemical molecules that are capable of initiating a free radical reaction and pendent bioactive groups and wherein the crosslinked matrix promotes tissue growth between the tissue site and the medical device.

9. A coated medical device comprising:
an implantable medical device with a surface having sufficient porosity to permit tissue growth in vivo, and
a matrix-forming system positioned upon the medical device and configured to promote tissue growth between a host tissue site and the medical device, wherein the matrix-forming system includes a multifunctional polymerization initiator and a polymer backbone having pendent polymerizable groups wherein the multifunctional polymerization initiator is a polymer bound initiator that comprises a polymeric core with pendent chemical molecules that are capable of initiating a free radical reaction and pendent chemical molecules capable of reducing immediate and chronic adverse reactions to the medical device.

10. The method of claim 8, wherein the adverse reactions comprise absorbance of undesirable proteins.

11. The method of claim 8, wherein the backbone comprises polyethylene glycol.

12. The method of claim 8, wherein the polymerizable groups comprise acrylates.

13. The method of claim 1, wherein the multifunctional polymerization initiator comprises a photoreactive group and two or more bioactive groups.

14. The method of claim 13, wherein the photoreactive group is selected from the group consisting of acetophenone, benzophenone, anthraquinone, quinone, anthrone, anthrone-like heterocycles and combinations thereof.

15. The method of claim 13, wherein the bioactive groups are selected from the group consisting of cell attachment factors, growth factors, antithrombotic factors, binding receptors, ligands, enzymes, antibiotics, nucleic acids, lysine, and fatty acids.

* * * * *